United States Patent [19]

Hess

[11] Patent Number: 4,537,507
[45] Date of Patent: Aug. 27, 1985

[54] DUAL BEAM MAXIMUM INTENSITY LASER SIZING SYSTEM

[75] Inventor: Cecil Hess, Irvine, Calif.

[73] Assignee: Spectron Development Laboratories, Inc., Costa Mesa, Calif.

[21] Appl. No.: 434,905

[22] Filed: Oct. 18, 1982

[51] Int. Cl.³ .............................................. G01N 15/02
[52] U.S. Cl. ..................................... 356/336; 356/28.5
[58] Field of Search ...................... 356/28.5, 336, 338; 250/222.2

[56] References Cited

U.S. PATENT DOCUMENTS

| | | | |
|---|---|---|---|
| 4,329,054 | 5/1982 | Bachalo | 356/336 |
| 4,387,993 | 6/1983 | Adrian | 356/336 |

FOREIGN PATENT DOCUMENTS 0035437  9/1981  European Pat. Off. ............ 356/336

OTHER PUBLICATIONS

Bachalo "Method for Measuring the Size and Velocity of Spheres by Dual-Beam Light Scatter Interferometry" *Applied Optics,* vol. 19, No. 3, pp. 363–367.

*Primary Examiner*—Davis L. Willis
*Assistant Examiner*—Matthew W. Koren
*Attorney, Agent, or Firm*—Blakely, Sokoloff, Taylor & Zafman

[57] ABSTRACT

An apparatus and method for determining the size and velocity of particles, droplets and the like is disclosed. Laser beams of the same wavelength having different diameters are caused to cross and form an interference pattern. The scattered light caused by particles, droplets or the like passing through the interference pattern is sensed by a collection means. The scattered signal is passed through a high pass filtering means to isolate Doppler (AC) components, and a low pass filtering means to isolate a DC pedestal signal. The AC signal is processed to provide the velocity, and the DC signal is processed to provide the size of the particle, droplet or the like. The position of the AC Doppler components in the scattered signal indicates the position of the particle in the cross-section of the larger diameter beam.

22 Claims, 5 Drawing Figures

DUAL BEAM MAXIMUM INTENSITY LASER SIZING SYSTEM

BACKGROUND OF THE INVENTION

1. Field

The present invention relates to the field of determining the parameters of particles, droplets or the like, and more particularly, to the determination of particle size and velocity using laser light scattering.

2. Art Background

There has long been a need to measure particle and droplet size in sprays, planetary atmospheres, combustion processes and the like. Such measurements are useful in aircraft icing studies, planetary studies, fuel analysis, and numerous combustion and nozzle applications. A number of techniques employing laser light scattering have been developed to determine the size and/or velocity of particles, droplets or the like.

In one system, commonly referred to as a particle sizing interferometer, a pair of laser beams of equal size and intensity are caused to cross and form a sample volume. An interference pattern between the beams is established by this crossing, and particles moving through this volume scatter light in proportion to the spacially varying light intensity within the interference pattern. From the scattered light, information concerning both the particle size and velocity can be computed. The particle's size is determined from a visibility factor (V) which is a function of the relative maximum and minimum intensity of the received scattered signal. A more detailed explanation of this interferometric technique is given in "On Line Particle Monitoring Instruments", by Bachalo, Geffken and Weth, 1978 *Symposium on Instrumentation and Control for Fossil Demonstration Plants,* June 19-21, 1978; and U.S. Pat. No. 4,329,054, which issued on May 11, 1982. However, the determination of particle size based on a visibility function may give rise to significant errors. In the case where $D/\delta$ (where $D$ = the particle diameter and $\delta$ = the fringe spacing) is in the range of 0.08-0.24, a 10 percent error in determining the visibility factor potentially results in a 300 percent size error.

The correlation between scattered light intensity and particle size has long been used for sizing small particles carried in a fluid. Various techniques have been devised in an attempt to utilize the intensity of the scattered signal as a direct measurement of particle size. These techniques are generally intrusive, in that that samples are drawn into the sizing apparatus and cannot be used to measure external sprays or the like. However, there exist non-intrusive techniques which utilize probability inversion methods to convert the apparent size of particles based on their absolute intensity into actual particle sizes. In addition, the particle's velocity may be determined from the fringe spacing of the detected interference signal. See, Yule, Chigier, "Particle Size and Velocity Measurement by Laser Anemometry", 15th *Aerospace Sciences Meeting,* (AIAA, Jan. 24-26, 1977). However, systems of this type base the determination of particle size on a number of assumptions used in the development of the probability function, in order to convert the apparent particle size into an "actual" particle size.

Since most laser beams have Gaussian intensity profiles over their cross section, a particle traversing the middle of a beam will scatter more light than if the particle crosses through the outer portion ("tail") of the beam. Therefore, in order to achieve a true intensity versus size correlation it must be determined if a certain scattered signal level corresponds to a small particle crossing through the central portion of the beam, or large particle crossing through the tail. Inasmuch as systems such as that disclosed by Yule and Chigier cannot determine if a particle has passed through the central portion of the laser beam, their analysis can only provide a statistical distribution of the size and velocity of the many particles which pass through their device.

Moreover, the sensed information from the laser interference pattern may represent scattering associated with multiple droplets. In the present invention, this multiplicity is significantly less of a problem than in prior art methods (for example visibility based systems) which rely on the quality of the phase front of the laser beams. A number of systems have been developed to insure that only single particles, droplets or the like passing through the central portion of the laser beam interference pattern are analyzed (See U.S. Pat. No. 4,329,054). However, these systems do not preserve the information needed in order to determine a particular particle's size and velocity simultaneously.

As will be described, the present invention overcomes the disadvantages associated with prior art systems, and discloses a technique which insures that the parameters associated with a particle are determined only if the particle lies within the central portion of the laser beam for any given measurement. In addition, the present invention provides a means whereby both the size of the particle, droplet or the like as well as its velocity may be simultaneously determined.

SUMMARY OF THE INVENTION

An apparatus and method for determining the size and velocity of particles, droplets or the like employing laser light scattering is disclosed. A laser generation means for generating a pair of coherent laser beams of the same wavelength is provided. These beams have different diameters and are directed and focused along an axis, and caused to cross the axis at a given angle to establish an interference pattern. The interference pattern of fringes define a region of substantially uniform intensity within the larger diameter laser beam. A collection means for sensing the scattering caused by the particles, droplets or the like within the interference pattern is provided.

The position of Doppler (high frequency AC) components in the scattered signal is an indication of the particle's position within the larger diameter beam's Gausian intensity distribution, and thereby provides a means to insure that the particle of interest to be analyzed is situated within the central portion of the larger diameter beam. Thus, scattered signals are processed only if the signals contain proper Doppler modulation, inasmuch as only particles, droplets or the like within the central region of the larger diameter beam will generate such high frequency signals. The scattered signal is passed through a high pass filtering means to isolate the Doppler (AC) component of the scattered signal, which is then processed in a conventional manner to obtain the velocity of the particle, droplet or the like passing through the interference pattern. In addition, the scattered signal is passed through a low pass filtering means, in order to provide a pedestal (DC) signal representing the intensity distribution absent the Doppler component. This pedestal signal is then processed in a well known manner, in order to obtain the peak intensity of the light scattered from the larger beam and thereby the particle size using accepted intensity-size mathematical relationships.

In an alternate embodiment, a laser beam of a first color is provided along with a coincident laser beam of a second color having a smaller diameter than the first laser beam. A third beam having the same color as that of the second beam is directed so as to cross the smaller diameter beam within the larger first color beam, thereby providing fringes within the central region of the first color beam. First and second collection means for sensing the scattering caused by particles, droplets or the like in the interference pattern are provided. The first collection means is sensitive only to scattering of the first color laser beam and the second collection means is sensitive only to scattering of the second color laser beams. Thus, the AC Doppler component of the scattered signal may be directly measured without the necessity of filtering DC components from the scattered signal, and the DC pedestal signal may be directly sensed by the output of the second collection means. The alternate embodiment allows for independent adjustment of the intensity of the small and large beams, which permits in the largest possible Doppler and pedestal signals to be generated. Accordingly, detectability is increased along with the signal-to-noise ratio of the system, and error is thereby reduced.

BRIEF DESCRIPTION OF THE DRAWINGS

FIG. 6 is an alternate embodiment of the present invention, using laser beams of different colors in order to determine the size and velocity of a particles, droplets or the like.

DETAILED DESCRIPTION OF THE INVENTION

An apparatus and method for determining the size and velocity of particles, droplets or the like using laser light scattering is disclosed. In the following description for purposes of explanation, numerous details are set forth such as specific wavelengths, angles, frequencies, etc., in order to provide a thorough understanding of the present invention. However, it will be obvious to one skilled in the art that the invention may be practiced without these specific details. In other instances, well known components, structures and electrical processing means have not been described in detail in order not to obscure the present invention unnecessarily.

Figure 1:
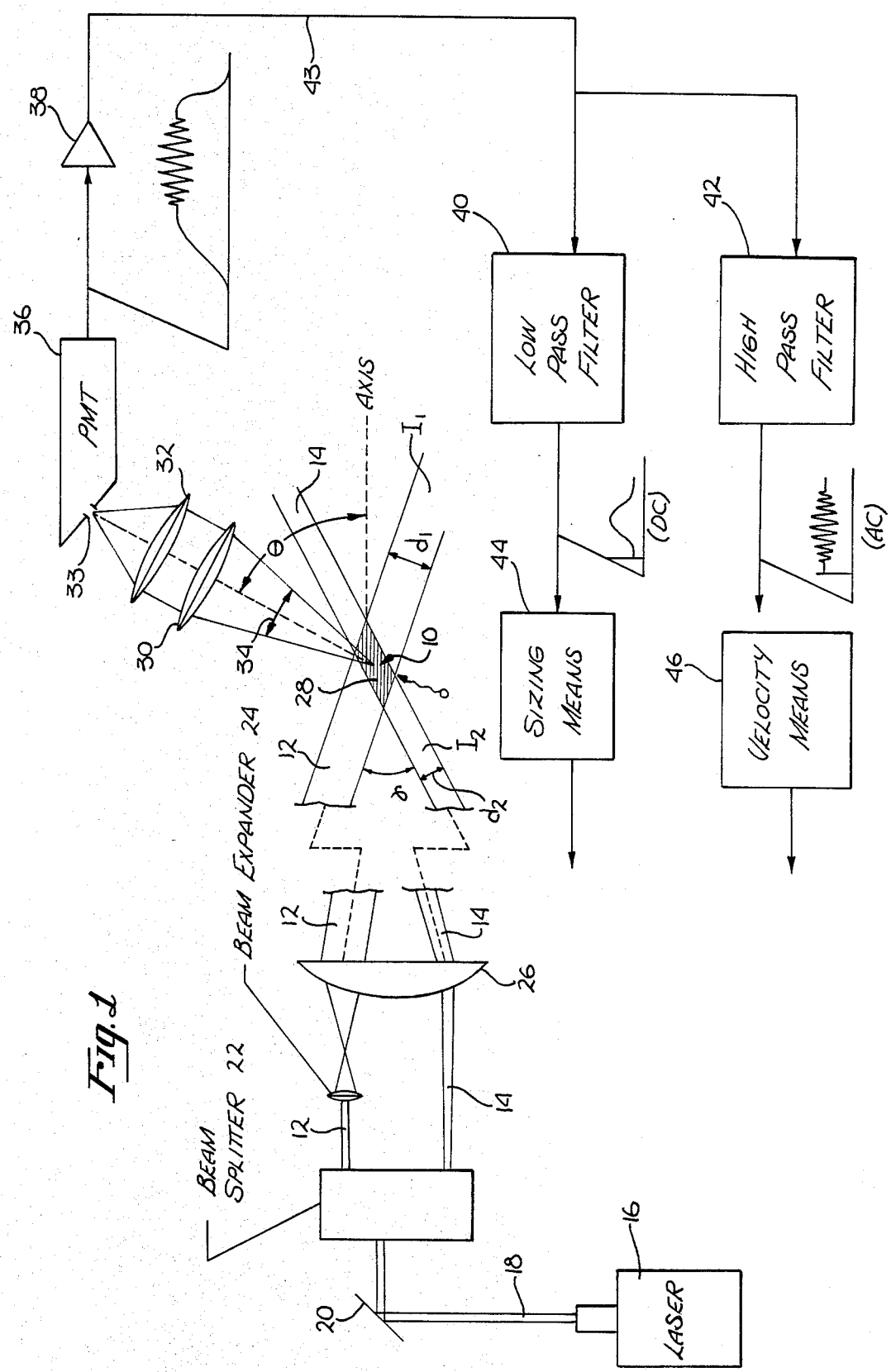
FIG. 1 is a diagrammatical representation of the presently preferred embodiment of the invention.

Referring now to FIG. 1, the apparatus for determining the size and velocity of particles, droplets or the like includes a sample volume 10. The sample volume 10 is defined as the overlap region of a first laser beam 12 having a diameter $D_1$, and a second laser beam 14 having a diameter $D_2$. As is illustrated, the diameter of the second beam is less than the diameter of the first beam, and the beams are caused to cross at an angle $\gamma$ with respect to an axis defined through the intersection of the two beams.

The laser beams employed by the present invention are generated, in the presently preferred embodiment, by a laser 16. The beam 18 from laser 16 is reflected off of a reflector 20 and passed through a beam splitter 22 thereby forming the first and second laser beams 12, and 14, respectively. Beam 12 is then passed through a beam expander 24 in order to enlarge its diameter, and then both beams 12 and 14 are passed through a focusing lens 26 which causes the beams to cross at the desired angle and form the sample volume 10. The beams 12 and 14 are of the same wavelength, but need not be of the same intensity.

The crossing of beams 12 and 14, as is well known, establishes the interference (fringes) pattern 28 within the sample volume 10. (Note that in FIG. 1, the beams 12 and 14 have been broken and then shown in enlarged form within the sample volume 10 in order to illustrate the interference pattern 28). These fringes define a region of substantially uniform intensity within the larger first beam 12. Particles, droplets or the like passing through the sample volume 10 scatter light in proportion to the spacially varying light intensity of the fringe pattern. As will be discussed, the scattered light through this pattern carries information concerning a particle's size and velocity. The scattering is sensed by a collection means which includes lenses 30 and 32, as well as an aperture 33, which defines a solid angle of collection 34 extending into the fringe pattern 28. The intersection between the image of the aperture 33 and the interference pattern of fringes 28 defines a probe volume. In practice, it has been found that a rectangular aperture minimizes aperture edge effects.

The light scattered within the solid angle 34 by particles, droplets or the like passing through the probe volume is collected and focused by lenses 30 and 32 onto a photomultiplying tube 36. The electrical output of this tube passes through a preamplifier 38 on line 43, and is coupled to a low pass filter means 40 and a high pass filter means 42. As will be discussed more fully below, the low pass filter means 40 filters the scattered signal on line 43 and provides a DC pedestal signal representative of the intensity profile of the larger diameter beam 12. This pedestal signal is then coupled to a sizing means 44 which then determines the size of the particle, droplet or the like passing through the probe volume. Various well known sizing techniques may be used in order to determine the size of the particular particle, droplet or the like, from the pedestal signal, such as for example Mie scattering theory.

Similarly, the scattered signal on line 43 is coupled to high pass filter means 42, which provides an output representative of high frequencies within the scattered signal which fall within a predetermined range. As illustrated, high pass filter means 42 provides a signal representative of high frequency Doppler (AC) components within the collected scattered signal. These Doppler signals are then coupled to a velocity means 46, which in a well known manner, determines the velocity of the particle, droplet or the like which generated the particular Doppler fringes. It will be appreciated, that standard techniques may be employed in order to determine the velocity of a particle, droplet or the like from the Doppler fringes as is commonly done in standard laser Doppler velocimeter systems.

Figure 2:
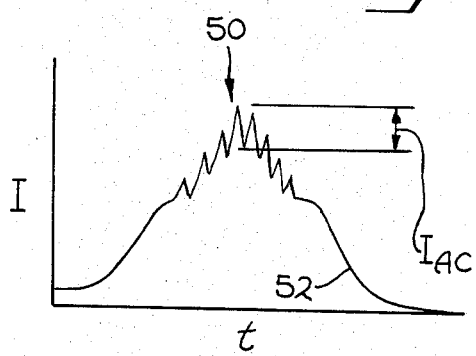
FIG. 2 graphically illustrates a sample received scattered signal from the present invention.

Referring now to FIG. 2, the present invention's use of laser beams having different diameters and intensities in order to generate signals indicative of the size and velocity of a particle, droplet or the like, while insuring that the particle passes through the central portion of the first beam 12 will be described. The intensity of the light scattered by a particle of diameter d from each of the laser beams 12 and 14 can be expressed as:

$$I_{12} = K_o d^2 I_{o12} e^{\frac{-8}{d_{12}^2}(X^2 + Y^2)}$$

$$I_{14} = K_o d^2 I_{o14} e^{\frac{-8}{d_{14}^2}(X^2 + Y^2)}$$

where:

$K_o$ = Mie scattering coefficient =

$$\frac{2\pi^2}{\lambda^2} \int_{A_{Lens}} |E(\theta,M)| D(\theta) dA$$

d = diameter of particle, droplet or the like,
$d_{12}$ = diameter of beam 12 at the sample volume,
$d_{14}$ = diameter of beam 14 at the sample volume,
$\lambda$ = wavelength of beams 12 and 14
D = divergence,
M = Index of refraction of the droplet,
$\theta$ = Angle between the collecting means and the bisector of the angle between beams 12 and 14,
$I_o$ = center intensity of the beams,
X,Y = position of particle, droplet or the like in probe volume 10, where the X direction is normal to fringes 28, and the origin lies at the center of volume 10, such that the total intensity scattered from the two beams 12 & 14 may be expressed as:

$$I_T = I_{12} + I_{14} + 2\sqrt{I_{12}I_{14}} \cos B$$

where

B = phase angle of the interference pattern.

As illustrated in FIG. 2, the scattered signal which is received by photomultiplier tube 36 is generally of a Gaussian form. However, as shown, when a particle droplet or the like, passed through the probe volume, the signal includes high frequency (AC) Doppler fringes 50. Thus, the received scattered signal comprises a combination of Doppler components and a DC pedestal signal 52. As previously discussed, the present invention isolates each of these respective signal components by passing the scattered signal through high pass filter means 42 and low pass filter means 40.

Figure 5:
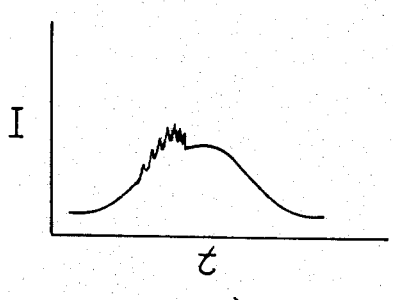
FIG 5 graphically illustrates the position of Doppler components in the received scattered signal if a particle, droplet or the like is not within the central portion of the larger diameter laser beam.
Figure 5:
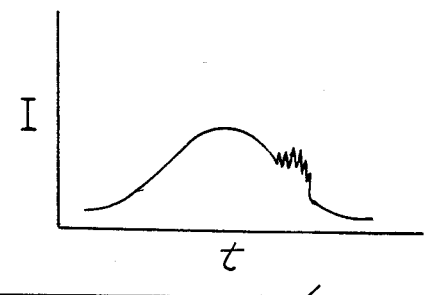

It will be appreciated by one skilled in the art that the position of AC Doppler fringes in the scattered signal is indicative of the position of a particle, droplet or the like in larger diameter beam 12. As shown in FIG. 5, if the particle to be examined does not lie within the central portion of the beam 12, the Doppler fringes produced by the particle will not lie within the maximum intensity range of the received scattered signal. Thus, it will be apparent that the present invention provides a simple and straightforward means for insuring that a particle, droplet or the like is detected and analyzed only if it passes through the central portion of beam 12.

By providing appropriate detection circuitry and optics, the determination of a particle's size and velocity will occur only if the particle crosses the center of the larger beam, thereby insuring a known incident beam intensity. Thus, the numerous problems associated with prior art devices in calculating size based on intensity are obviated, inasmuch as the information needed to determine the position of a particle in beam 12 is included as part of the received scattered signal. Accordingly, the present invention does not require the numerous assumptions and statistical correlations needed for prior art intensity to size transformations, inasmuch as a particle will only be measured if it lies within the central portion (the region of maximum intensity) of laser beam 12.

Figure 3:
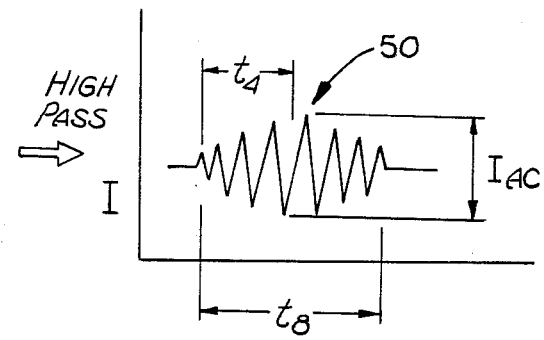
FIG. 3 graphically illustrates the present invention's use of filters to isolate the Doppler signal found in the scattered signal of FIG. 2.

As shown in FIG. 2, the scattered signal on line 43 is passed through a high pass filter means 42 to isolate the Doppler AC fringes (see FIG. 3). The intensity of the AC component may be expressed as:

$$I_{AC} = 2\sqrt{I_{12}I_{14}} \; V$$

where V = visibility factor

The Doppler AC signal is then utilized to determine the velocity of the particle, droplet or the like, as is common in standard laser doppler velocimeter systems.

Figure 4:
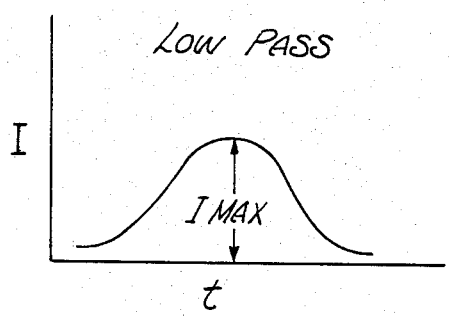
FIG. 4 graphically illustrates the present invention's use of filters to isolate the pedestal components from the scattered signal of FIG. 2.

Similarly, the scattered signal is passed through low pass filter means 40 to isolate the DC pedestal component in order to determine the maximum intensity distribution of the scattered signal (See FIG. 4). The maximum peak intensity of the scattered signal received by the photomultiplier tube 36 can be expressed as:

$$I_{peak} = (I_{12} + I_{14})|_{y=x=o}(1+V)$$

This $I_{peak}$ signal is then passed through the low pass filter (40) to obtain the maximum pedestal intensity of the larger beam 12. This maximum intensity is given by:

$$I_{max} = K_o d^2 I_{o12}$$

It will be appreciated, that inasmuch as the output from the low pass filter means reflects the maximum intensity of a particular particle, droplet or the like within the central portion of beam 12, it is a simple matter to directly determine a particle's size using well known intensity-size relationships, such as Mie theory. In fact, a look-up table in a digital memory may be utilized which directly relates the maximum intensity to the corresponding particle size. Since the mathematical relationships and size-intensity transforms are well known in the art, they will not be recited in this Patent.

Thus, the present invention's use of larger beam 12 and smaller beam 14 in conjunction with the filtering means 40 & 42, permits the simultaneous determination of a particle's size and velocity using techniques well known in the art, by insuring that the particle traverses through the central portion of the larger beam 12. Accordingly, the present invention does not require the use of statistical approximations and assumptions required in prior art systems. Moreover, it will be appreciated that the range of sizes and velocities of sensed particle's may be adjusted by proper variation of the relative intensities of beams 12 and 14, as well as the specifications of the collection system. In practice, the present invention can typically size particles within a 20 to 1 size range, and a velocity range of 6 to 1. Inasmuch as the present invention determines particle size based on scattered signal intensity which is readily ascertainable, a small error in the determination of intensity results in a small error in size determination. For example, assuming a very large 50% error in the intensity determination, a 30% error in size would result. Thus, it will be appreciated that for a more realistic intensity error of say 10%, the error in size would be very small and still within very acceptable limits.

Figure 6:
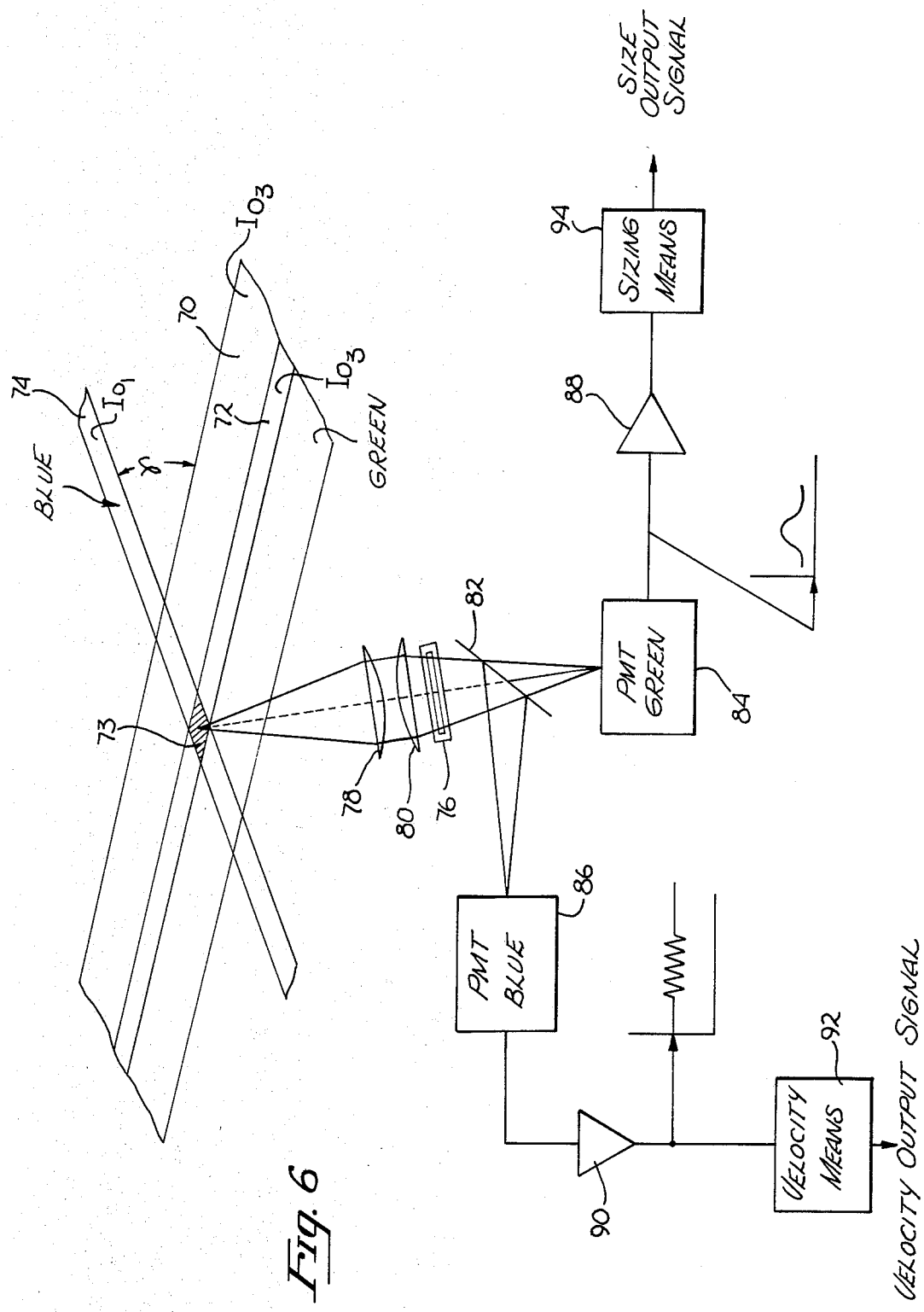

Referring now to FIG. 6, an alternate embodiment of the present invention is disclosed which utilizes different color laser beams in order to facilitate the separation of AC and DC signal components. A first color laser beam 70 is provided with a parallel and coincident second color beam 72 disposed within the first beam. For purposes of illustration, the beams have been colored such that the larger diameter beam is green and the smaller is blue. However, it will be appreciated that many color combinations between the two beams is possible.

A third laser beam 74 having the same color as that of beam 72 is provided such that it crosses beams 70 and 72 at a given angle $\gamma$ and generates fringes within a sample volume 73. It will be noted, that the intensity of each beam 70, 72 and 74 may be varied in order to maximize the scattered signals created by a particle, droplet or the like passing through the fringe pattern. A collection means is provided which, as in the embodiment of FIG. 1, includes an aperture 76, and lenses 78 and 80. A partially reflecting mirror 82 is provided such that the scattered light collected by the collection means is transmitted to a first photomultiplier tube (PMT) 84 and a second photomultiplier tube 86. It will be noted that although in the embodiments illustrated in FIGS. 1 and 4 photomultiplier tubes are used, that other sensing means such as detector diodes may also be utilized.

The first PMT 84 has an interference filter which transmits only light having the color of the first color beams 70, and the second PMT 86 has an interference filter which transmits only light having the color of the second and third laser beams 72 and 74. The signals received by each PMT are amplified by preamplifiers 88 and 90, respectively. The signals from PMT 86 are then coupled directly to a velocity means 92 which, as discussed in connection with FIG. 1, determines the velocity of the particle, droplet or the like using standard laser Doppler velocimeter techniques. Similarly, the signals from PMT 84 are directly coupled to sizing means 94, which as previously discussed, determines a particle's size from the intensity of the received scattered signal. Thus, it will be apparent that the use of multi-color beams, as illustrated in FIG. 6, eliminates the need to separate the signals from both color beams, inasmuch as each signal is sensed separately based on its wavelength. The use of multi-color beams permits independent adjustment of the intensity of the small and large diameter beams, which allows the user to obtain the largest Doppler and pedestal signals to be generated. Accordingly, detectability is increased as well as the signal to noise ratio of the system, and error is thereby reduced.

Thus, an improved laser interformeter system for determining the size and velocity of particles, droplets and the like, has been disclosed. The present invention's use of laser beams having different diameters, provides a means which allows the measurement of a particle's size based on the actual intensity of the scattered signal. In addition, the present invention provides a means to insure that a particle to be measured lies within the central portion of the larger diameter beam, by detecting the presence of Doppler fringes in the scattered signal. The velocity of the particle may be measured using standard Doppler techniques from the Doppler fringes.

Although the present invention has been described with reference to FIGS. 1-6, it will be understood that the Figures are for illustration only and should not be taken on limitations upon the invention.

I claim:

1. In an apparatus for measuring or sensing parameters associated with particles, droplets or the like, employing laser scattering, a method for determining when a particle, droplet or the like has crossed the central portion of a first laser beam, comprising the steps of:
    (a) generating a second laser beam, said second laser beam having a smaller diameter than said first laser beam;
    (b) directing said laser beams along an axis and causing said beams to cross said axis at a known angle in order to establish an interference pattern within the area defined by the intersection of said first and second laser beams;
    (c) sensing the scattered signal of said beams caused by a particle, droplet or the like passing through said interference pattern;
    (d) filtering said signal such that only signal components having frequencies within a predetermined range are permitted to pass;
    (e) detecting the presence of Doppler fringes in said filtered signal, thereby indicating that said particle, droplet or the like has crossed the central portion of said first laser beam.

2. The method as defined by claim 1 wherein said filtering step includes passing said scattered signal through a high pass filter means such that substantially only said Doppler fringes are permitted to pass therethrough.

3. The method as defined by claim 2 wherein said generating step includes splitting said first beam to form said second laser beam and expanding said first beam such that said second beam has a smaller diameter than said first beam.

4. The method as defined by claim 1 wherein said first and second laser beams are of the same wavelength.

5. The method as defined by claim 4 wherein said sensing step includes collecting said scattered signal using a lens and amplifying said signal using photomultiplier means.

6. In an apparatus for measuring or sensing parameters associated with particles, droplets, or the like, employing laser scattering, an improvement for determining when a particle, droplet, or the like has crossed the central portion of a first laser beam, comprising:
    laser generation means for generating a second laser beam, said second laser beam having a smaller diameter than said first beam;
    light directing means for directing said laser beams along an axis and for causing said pair of laser beams to cross said axis at a known angle to establish an interference pattern within the area defined by the intersection of said first and second beams;

sensing means for sensing the scattered signal of said beams caused by a particle, droplet or the like passing through said interference pattern;

filtering means coupled to said sensing means for filtering said signal such that only signal components having frequencies within a predetermined range are permitted to pass;

detecting means coupled to said filtering means for detecting the presence of Doppler fringes in said filtered signal, thereby indicating that said particle, droplet or the like has crossed the central portion of said first laser beam.

7. The apparatus as defined by claim 6 wherein said filtering means comprises a high pass filter such that substantially only Doppler fringes within said predetermined range are permitted to pass.

8. The apparatus as defined by claim 7 wherein said sensing means includes a collecting lens and photomultiplier tube.

9. The apparatus as defined by claim 8 wherein said first and second laser beams are of the same wavelength.

10. The apparatus as defined by claim 9 wherein said laser generation means comprises a beam splitter and beam expander in the path of said first beam, such that said second beam is formed and the diameter of said first beam exceeds the diameter of said second beam.

11. An apparatus for determining the size of particles, droplets or the like, employing laser scattering, comprising:

laser generation means for providing first and second laser beams, said first beam having a greater diameter than said second beams;

light directing means for directing said laser beams along an axis and for causing said pair of laser beams to cross said axis at a given angle to establish an interference pattern between said pair of beams;

collection means for sensing the scattered signal of said beams caused by a particle, droplet or the like in said interference pattern;

filter means coupled to said collection means for filtering said scattered signal and for providing a pedestal (DC) signal representative of the intensity of said scattered signal;

sizing means coupled to receive said pedestal signal to establish the size of said particle, droplet or the like;

whereby the size of said particle, droplet or the like is determined.

12. The apparatus is defined by claim 11 wherein said filter means includes a low pass filter to obtain said pedestal signal.

13. An apparatus for determining the velocity of particles, droplets and the like, employing laser scattering, comprising:

laser generation means for providing first and second laser beams, said first beam having a greater diameter than said second beam;

light directing means for directing said laser beams along an axis and for causing said pair of laser beams to cross said axis at a given angle to establish an interference pattern between said pair of beams;

collection means for sensing the scattered signal of said beams caused by a particle, droplet or the like in said interference pattern;

filter means coupled to said collection means for filtering said scattered signal and providing a high frequency signal representative of high frequency Doppler (AC) signal components of said scattered signal;

velocity means coupled to receive said high frequency Doppler signal for determining the velocity of said particle, droplet or the like;

whereby the velocity of said particle, droplet or the like is determined.

14. The apparatus is defined by claim 13 wherein said filter means includes a high pass filter to obtain said Doppler signals.

15. An apparatus for determining the size and velocity of particles, droplets and the like, employing laser scattering, comprising:

laser generation means for providing first and second laser beams, said first beam having a greater diameter than said second beam;

light directing means for directing said laser beams along an axis and for causing said pair of laser beams to cross said axis at a given angle to establish an interference pattern between said pair of beams;

collection means for sensing the scattered signal of said beams caused by a particle, droplet or the like in said interference pattern;

filter means coupled to said collection means for filtering said scattered signal and providing high frequency signals representative of the high frequency Doppler (AC) signal components of said scattered signal, and a pedestal (DC) signal representative of the intensity of said scattered signal;

sizing means coupled to receive said pedestal signal to establish the size of said particle, droplet or the like;

velocity means coupled to receive said high frequency Doppler signal for determining the velocity of said particle, droplet or the like;

whereby both the size and velocity of said particle, droplet or the like is determined.

16. The apparatus as defined by claim 15 wherein said filter means includes a high pass filter to obtain said Doppler signals and a low pass filter to obtain said pedestal signal.

17. The apparatus as defined by claim 11 or 15 wherein said collection means includes a lens and at least one photomultiplier means.

18. The apparatus as defined by claim 17 wherein said first and second laser beams have the same wavelength.

19. The apparatus as defined by claim 18 wherein said first and second laser beams are formed from the same generation means, said second beam being formed by passing said first beam through a beam splitter, the diameter of said first beam being enlarged by a beam expander.

20. A method for sizing a particle, droplet or the like, employing laser scattering, which comprises the steps:

generating first and second laser beams, said first beam having a greater diameter than said second beam;

directing and focusing said first and second laser beams along an axis and causing said first and second beams to cross said axis to establish an interference pattern between said beams the intensity of said mixed beams being described by the following relationship;

$$I_T = I_{12} + I_{14} + 2\sqrt{I_{12}I_{14}} \cos B$$

where,

B = phase angle of said interference pattern,
$I_{12}$ = intensity of first laser beam, $I_{14}$ = intensity of second laser beam, sensing resulting scattered signals of said first and second laser beams caused by a particle, droplet or the like passing through said interference pattern;

low pass filtering said scattering signal to determine the intensity of the pedestal signal;

determining the size of said particle, droplet or the like from said pedestal signal.

21. A method for determining the velocity of a particle, droplet or the like employing laser scattering, which comprises the steps of:

generating first and second laser beams, said first beam having a greater diameter than said second beam;

directing and focusing said first and second laser beams along an axis and causing said first and second beams to cross said axis to establish an interference pattern between said beam the intensity of said mixed beams being described by the following relationship;

$$I_t = I_{12} + I_{14} + 2\sqrt{I_{12}I_{14}} \cos B$$

where,

B = phase angle of said interference pattern, $I_{12}$ = the intensity of the first laser beam, $I_{14}$ = the intensity of the second laser beam, sensing resulting scattered signals of said first and second laser beams caused by a particle, droplet or the like passing through said interference pattern;

high pass filtering said scattered signals to determine the Doppler (AC) component of said intensity from the following relationship;

$$I_{ac} = 2\sqrt{I_{12}I_{14}} \; V$$

where, V = signal visibility, determining the velocity of said particle, droplet or the like from said Doppler component;

whereby the velocity of the particle, droplet or the like passing through said interference pattern is determined.

22. A method for determining the size and velocity of a particle, droplet or the like, employing laser scattering which comprises the steps:

generating first and second laser beams, said first beam having a greater diameter than said second beam;

directing and focusing said first and second laser beams along an axis and causing said first and second beams to cross said axis to establish an interference pattern between said beams; the intensity of said mixed beams being described by the following relationship;

$$I_t = I_{12} + I_{14} + 2\sqrt{I_{12}I_{14}} \cos B$$

where, $I_{12}$ = intensity of first laser beam, $I_{14}$ = intensity of second laser beam, B = phase angle of said interference pattern, sensing resulting scattered signals of said first and second laser beams caused by a particle, droplet and the like passing through said interference pattern;

high pass filtering said scattered signals to determine the Doppler (AC) component of said intensity from the following relationship;

$$I_{ac} = 2\sqrt{I_{12}I_{14}} \; V$$

where, V = signal visibility determining the velocity of said particle, droplet or the like from said Doppler component;

low pass filtering said scattering signal to determine the intensity of the pedestal signal;

determining the size of said particle, droplet or the like from said pedestal signal.

* * * * *